(12) United States Patent
Kim

(10) Patent No.: US 10,578,520 B2
(45) Date of Patent: Mar. 3, 2020

(54) PRETREATMENT APPARATUS AND METHOD FOR ANALYSING AIR POLLUTION DETECTION

(71) Applicant: KONKUK UNIVERSITY INDUSTRIAL COOPERATION CORP, Seoul (KR)

(72) Inventor: Jo-Chun Kim, Seoul (KR)

(73) Assignee: KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 113 days.

(21) Appl. No.: 15/570,547

(22) PCT Filed: Feb. 29, 2016

(86) PCT No.: PCT/KR2016/001978
§ 371 (c)(1),
(2) Date: Dec. 18, 2017

(87) PCT Pub. No.: WO2016/175440
PCT Pub. Date: Nov. 3, 2016

(65) Prior Publication Data
US 2018/0143105 A1    May 24, 2018

(30) Foreign Application Priority Data

Apr. 30, 2015   (KR) .................. 10-2015-0062003
Apr. 30, 2015   (KR) .................. 10-2015-0062008

(51) Int. Cl.
*G01N 1/22*    (2006.01)
*G01N 1/42*    (2006.01)
*G01N 1/44*    (2006.01)

(52) U.S. Cl.
CPC ............... *G01N 1/22* (2013.01); *G01N 1/42* (2013.01); *G01N 1/44* (2013.01); *Y02A 50/2354* (2018.01)

(58) Field of Classification Search
CPC ............... G01N 1/22; G01N 1/42; G01N 1/44
(Continued)

(56) References Cited

U.S. PATENT DOCUMENTS

2011/0159596 A1* 6/2011 Keinan ............... G01N 1/2211
                                                  436/52
2013/0174577 A1* 7/2013 Brija .................... F25B 21/04
                                                  62/3.2
2015/0233614 A1* 8/2015 Kindt .................. B01L 7/52
                                                  62/3.3

FOREIGN PATENT DOCUMENTS

JP    3029706 U     10/1996
JP    09-215906 A    8/1997
(Continued)

OTHER PUBLICATIONS

English translation of Haruo JP3029706 from jplatpat, accessed Jul. 19, 2019.*

(Continued)

*Primary Examiner* — Nimeshkumar D Patel
*Assistant Examiner* — Jean F Morello
(74) *Attorney, Agent, or Firm* — Novick, Kim & Lee, PLLC; Jae Youn Kim

(57) ABSTRACT

The present invention relates to a preprocessing apparatus and a preprocessing method for measuring and analyzing air pollution, and provides the preprocessing apparatus and the preprocessing method, in which there is included a cyclone main body, a block made of aluminum or copper and provided at an outer circumferential edge of the cyclone main body, and a cooling means surrounding the block, such that contaminated gas introduced into the cyclone main body (Continued)

is cooled within a predetermined range, and as a result, it is possible to remove moisture contained in combustion gas by crystallizing the moisture, and to separate particulate matters from the combustion gas based on a cyclone principle.

4 Claims, 13 Drawing Sheets

(58) Field of Classification Search
USPC .................................................. 73/863.11
See application file for complete search history.

(56) References Cited

FOREIGN PATENT DOCUMENTS

| | | | |
|---|---|---|---|
| JP | 2005131509 A | * | 5/2005 |
| KR | 10-0436358 B1 | | 9/2004 |
| KR | 2006-0039465 A | | 5/2006 |
| KR | 10-0823947 B1 | | 4/2008 |

OTHER PUBLICATIONS

English translation of Kang KR100823947 description from espacenet. com, accessed Jul. 23, 2019.*
English translation of byung JP2005131509 abstract from espacenet. com, accessed Jul. 23, 2019.*

* cited by examiner

PRETREATMENT APPARATUS AND METHOD FOR ANALYSING AIR POLLUTION DETECTION

TECHNICAL FIELD

The present invention relates to a preprocessing apparatus and a preprocessing method for analyzing air pollution, and more particularly, a preprocessing apparatus and a preprocessing method for measuring and analyzing air pollution, which are capable of effectively removing moisture and particulate matters to be measured and contained in combustion gas by adjusting a temperature of the combustion gas to a predetermined range, cooling the combustion gas, and thus inducing crystallization of moisture contained in the combustion gas.

BACKGROUND ART

Our natural environment has been increasingly destroyed due to urbanization, an increase in population, reckless destruction of nature, and the like. In particular, environmental pollution, which becomes a serious issue along with a rapid industrial development, is not a problem that only affects some countries, but it is no exaggeration to say that the environmental pollution is a problem that all of the countries in the world need to seriously worry about and cope with.

As a solution for solving the problem of the environmental pollution, developments should be performed on technologies of inhibiting emission of pollutants or removing pollutants inevitably discharged.

Among the technologies, an allowable emission standard for each emission source is defined and emission of pollutants is managed and regulated in order to inhibit emission of pollutants, and in general, emission monitoring is performed to check the amount of discharged pollutants and concentration of the pollutants, and this emission monitoring is considered as a very important factor in a field of prevention of environmental pollution.

In particular, an apparatus for monitoring emission of air pollutants produced by combustion of fossil fuel or various types of manufacturing processes causing environmental pollution usually uses a measurement method performed based on optical instruments. However, there are many cases in which it is difficult for a monitoring device to exactly recognize names of substances or concentration of air pollutants contained in combustion gas because of moisture or particulate matters contained in gaseous substances to be measured.

Therefore, to exactly recognize pollutants and concentration of the pollutants, it is necessary to remove moisture or particulate matters that make it difficult to perform measurement or analysis, and then to introduce the combustion gas into a measurement device, and in some instances, a filter is used as a preprocessing method. However, the filter may not only remove moisture or particulate matters, but also remove gaseous pollutants that need not be removed, that is, gaseous pollutants that are to be measured because moisture or particulate matters removed by the filter form another filter body, and as a result, there may be a problem in that it is difficult to exactly recognize pollutants.

Korean Patent Application Laid-Open No. 2006-0039465, which is the related art for solving the aforementioned problems, discloses a preprocessing apparatus for removing moisture. A glass tube for cooling and condensing moisture is provided at an inner circumferential edge in the preprocessing apparatus, and a cotton yarn layer for primarily removing moisture is further formed in the glass tube. Further, Korean Patent Application Laid-Open No. 2006-0039465 discloses that a Peltier trap for performing cooling, condensation, and thermal desorption is provided at a lower side of the preprocessing apparatus, such that the preprocessing apparatus having a moisture preprocessing means for analyzing air pollution operates to be heated to remove moisture after samples are completely captured by a sample capturing unit.

However, in the related art, it is possible to remove moisture contained in gas by using the Peltier trap, but it is still difficult to remove particulate matters, and as a result, there may occur an error related to an analysis result.

Further, in the related art, the Peltier trap is provided only at one side of the preprocessing apparatus, and as a result, there is a problem in that it is difficult to control a temperature, it is difficult to quickly perform cooling, and the apparatus is complicated because the separate glass tube needs to be provided.

DISCLOSURE

Technical Problem

The present invention has been made in an effort to solve the aforementioned problems, and an object of the present invention is to provide a preprocessing apparatus and a preprocessing method for measuring and analyzing air pollution, which are capable of ensuring reliability of a device for monitoring air pollutants by perfectly removing moisture and particulate matters contained in combustion gas, and capable of making it easy to perform maintenance such as a repair of the apparatus by simplifying configurations.

Technical Solution

As a first exemplary embodiment of the present invention for solving the aforementioned problems, a preprocessing apparatus for measuring and analyzing air pollution includes a cyclone main body 100 which includes a combustion gas inlet pipe 2 which is provided at one side of a cylindrical portion 1 and through which combustion gas including air pollutants to be measured is introduced, a preprocessed combustion gas discharge pipe 3 which is provided at an upper side of a center of the cylindrical portion 1, and a discharge port 8 which is provided on a conical portion 4 at a lower side of the cylindrical portion 1 and through which removed moisture and particulate matters are discharged, in which the cyclone main body 100 is provided with a cooling means for cooling the combustion gas including the air pollutants and a heating means for heating the combustion gas.

In addition, in the preprocessing apparatus for measuring and analyzing air pollution according to the first exemplary embodiment of the present invention, the cooling means may be first and second cooling Peltier elements 21 and 22, and the heating means may be a heating Peltier element 31.

In addition, in the preprocessing apparatus for measuring and analyzing air pollution according to the first exemplary embodiment of the present invention, a first cooling Peltier element 21 may be provided at one side of the inlet pipe 2, a heating Peltier element 31 may be provided at the other side of the inlet pipe 2, and second cooling Peltier elements 22 may be provided on the cylindrical portion 1 and the conical portion 4.

In addition, in the preprocessing apparatus for measuring and analyzing air pollution according to the first exemplary embodiment of the present invention, a block 40 made of aluminum or copper may be provided at an outer circumferential edge of the cylindrical portion 1 and the conical portion 4, and second cooling Peltier elements 22 may be provided at an outer circumferential edge of the block 40.

In addition, in the preprocessing apparatus for measuring and analyzing air pollution according to the first exemplary embodiment of the present invention, an inflow gas temperature sensor 5 may be provided on the inlet pipe 2 in order to measure a temperature of the combustion gas including the air pollutants, and a conical portion temperature sensor 6 may be further provided to measure a temperature at the conical portion 4.

In addition, in the preprocessing apparatus for measuring and analyzing air pollution according to the first exemplary embodiment of the present invention, a humidity sensor 7 may be further provided on the inlet pipe 2 in order to measure humidity of the combustion gas including the air pollutants.

In addition, the preprocessing apparatus for measuring and analyzing air pollution according to the first exemplary embodiment of the present invention may further include a protection box 60 which accommodates the cyclone main body; and a fiberglass layer 50 which fills a portion between the protection box 60 and the cyclone main body 100 for thermal insulation.

In addition, a preprocessing method for measuring and analyzing air pollution according to the first exemplary embodiment of the present invention may include: introducing combustion gas including air pollutants to be measured into a cyclone main body 100 (S100); crystallizing moisture contained in the combustion gas by cooling the moisture by a cooling means provided at an outer circumferential edge of the cyclone main body, and attaching some particulate matters to the crystallized moisture particles (S120); attaching or settling the crystallized moisture particles and the particulate matters attached to the moisture particles onto a wall surface at an inner circumferential edge of the cyclone main body, and discharging the combustion gas, from which the moisture particles and the particulate matters are removed, to an upper side of the cyclone main body (S140); introducing heated gas into the cyclone main body 100 and dissolving the crystallized moisture particles attached to the wall surface at the inner circumferential edge of the cyclone main body 100 (S160); and discharging the dissolved moisture and the particulate matters to the outside of the cyclone main body (S180).

In addition, in the preprocessing method for measuring and analyzing air pollution according to the first exemplary embodiment of the present invention, particulate matters, which are contained in the combustion gas and are not attached to the crystallized moisture particles, may be settled based on a cyclone principle.

In addition, in the preprocessing method for measuring and analyzing air pollution according to the first exemplary embodiment of the present invention, the cooling means provided at the outer circumferential edge of the cyclone main body may be a second cooling Peltier element 22, and a cooling temperature may be −20±10° C.

In addition, in the preprocessing method for measuring and analyzing air pollution according to the first exemplary embodiment of the present invention, in the introducing of the combustion gas into the cyclone main body, the temperature of the combustion gas may be maintained at 70±10° C., and the temperature range may be adjusted by a first cooling Peltier element 21 provided at one side of the inlet pipe 2 and a heating Peltier element 31 provided at the other side of the inlet pipe 2.

As a second exemplary embodiment of the present invention for solving the aforementioned problems, a preprocessing apparatus for measuring and analyzing air pollution includes: a combustion gas distribution unit 115 which has a first opening portion 110 formed in an upper surface and a plurality of second opening portions 120 formed in a lower surface, and has a vacant space portion; a cooling and heating block 200 which has a plurality of pierced cylindrical portions; a cooling block 300 which has cylindrical portions formed to correspond to the cylindrical portions of the cooling and heating block 200 and is positioned at a bottom side of the cooling and heating block 200; a bundle of pipes 400 which is inserted into the cylindrical portions 240 and 330 of the cooling and heating block 200 and the cooling block 300, and formed to have a length so that upper and lower end portions thereof protrude outward from the cooling and heating block 200 and the cooling block 300, such that the upper end portions thereof penetrate the cooling and heating block 200 and then are inserted into the second opening portions 120 of the combustion gas distribution unit 115 so as to be positioned in the vacant space portion of the combustion gas distribution unit 115; a socket unit 500 which accommodates the lower end portions of the bundle of pipes 400 which protrude outward from the cooling block 300; and a hood 600 which is coupled to the socket unit 500.

In addition, in the preprocessing apparatus for measuring and analyzing air pollution according to the second exemplary embodiment of the present invention, a third cooling Peltier element 210 may be provided at one side of the cooling and heating block 200, a second heating Peltier element 220 may be provided at the other side of the cooling and heating block 200, and a fourth cooling Peltier element 310 may be formed on the cooling block 300.

In addition, in the preprocessing apparatus for measuring and analyzing air pollution according to the second exemplary embodiment of the present invention, a shaped branch pipe 610 and a three-way valve 620 may be further provided at a bottom side of the hood 600.

In addition, in the preprocessing apparatus for measuring and analyzing air pollution according to the second exemplary embodiment of the present invention, a combustion gas inlet pipe 700 may be further provided to be inserted into the first opening portion 110 of the combustion gas distribution unit 10, and an inflow gas temperature sensor 710 may be further mounted at one side of the combustion gas inlet pipe 700 in order to measure a temperature of introduced gas.

In addition, in the preprocessing apparatus for measuring and analyzing air pollution according to the second exemplary embodiment of the present invention, a cooling and heating block temperature sensor 230 for measuring a temperature of the cooling and heating block 200 and a cooling block temperature sensor 320 for measuring a temperature of the cooling block 300 may be further mounted.

In addition, in the preprocessing apparatus for measuring and analyzing air pollution according to the second exemplary embodiment of the present invention, a second humidity sensor 130 for measuring humidity of gas introduced into the combustion gas inlet pipe 700 may be mounted in the combustion gas distribution unit 115.

In addition, the preprocessing apparatus for measuring and analyzing air pollution according to the second exemplary embodiment of the present invention may further include: a second protection box 800 which accommodates the combustion gas distribution unit 115, the cooling and heating block 200, the cooling block 300, and the hood 600; and a second fiberglass layer 900 which is accommodated in space portions between the second protection box 800, the combustion gas distribution unit 115, the cooling and heating block 200, the cooling block 300, and the hood 600.

A preprocessing method for measuring and analyzing air pollution according to the second exemplary embodiment of the present invention may include: a first step (S200) of introducing combustion gas including air pollutants to be measured into a combustion gas inlet pipe 700; a second step (S210) of distributing the combustion gas introduced into the combustion gas inlet pipe 700 to a bundle of pipes 400; a third step (S220) of cooling the gas distributed from the bundle of pipes 400 and crystallizing moisture contained in the combustion gas; and a fourth step (S230) of attaching the crystallized moisture particles to inner wall surfaces of the bundle of pipes 400.

In addition, in the preprocessing method for measuring and analyzing air pollution according to the second exemplary embodiment of the present invention, in the third step (S220) of crystallizing the moisture, particulate matters contained in the combustion gas may be attached when the moisture is crystallized or the particulate matters may be attached to the moisture that is already crystallized.

In addition, the preprocessing method for measuring and analyzing air pollution according to the second exemplary embodiment of the present invention may further include: a fifth step (S240) of dissolving the crystallized moisture particles attached to the inner wall surfaces of the bundle of pipes 400 by introducing heated gas after the fourth step (S230); and a sixth step (S250) of discharging the dissolved moisture to the outside.

In addition, the preprocessing method for measuring and analyzing air pollution according to the second exemplary embodiment of the present invention may further include a first of second step (S215) of adjusting a temperature of the combustion gas distributed to the bundle of pipes 400 to 70±10° C.

In addition, in the preprocessing method for measuring and analyzing air pollution according to the second exemplary embodiment of the present invention, a cooling temperature in the third step (S220) may be in a range of −20±10° C.

Advantageous Effects

The preprocessing apparatus and the preprocessing method for measuring and analyzing air pollution according to the first exemplary embodiment of the present invention cools combustion gas by using the cooling means and uses cyclone centrifugal force, and as a result, it is possible to remove particulate matters as well as moisture contained in the combustion gas, and thus to ensure reliability of a result of measuring air pollution. In addition, the cooling means and the heating means are provided at the outer circumferential edge of the cyclone main body, and as a result, it is possible to easily adjust a temperature of combustion gas.

Further, according to the second exemplary embodiment of the present invention, it is possible to remove moisture contained in combustion gas by using a simple temperature difference, thereby achieving simplification and reliability of the apparatus. In addition, in the present invention, a temperature of combustion gas is adjusted by using the Peltier effect, and as a result, the temperature of the combustion gas is easily adjusted, and an economic effect is expected.

DESCRIPTION OF DRAWINGS

The following drawings serve to further understand the technical spirit of the present invention together with the detailed description of the present invention, and the present invention should not be interpreted as being limited to the items illustrated in the drawings.

DESCRIPTION OF MAIN REFERENCE NUMERALS OF DRAWINGS

Figure 1:
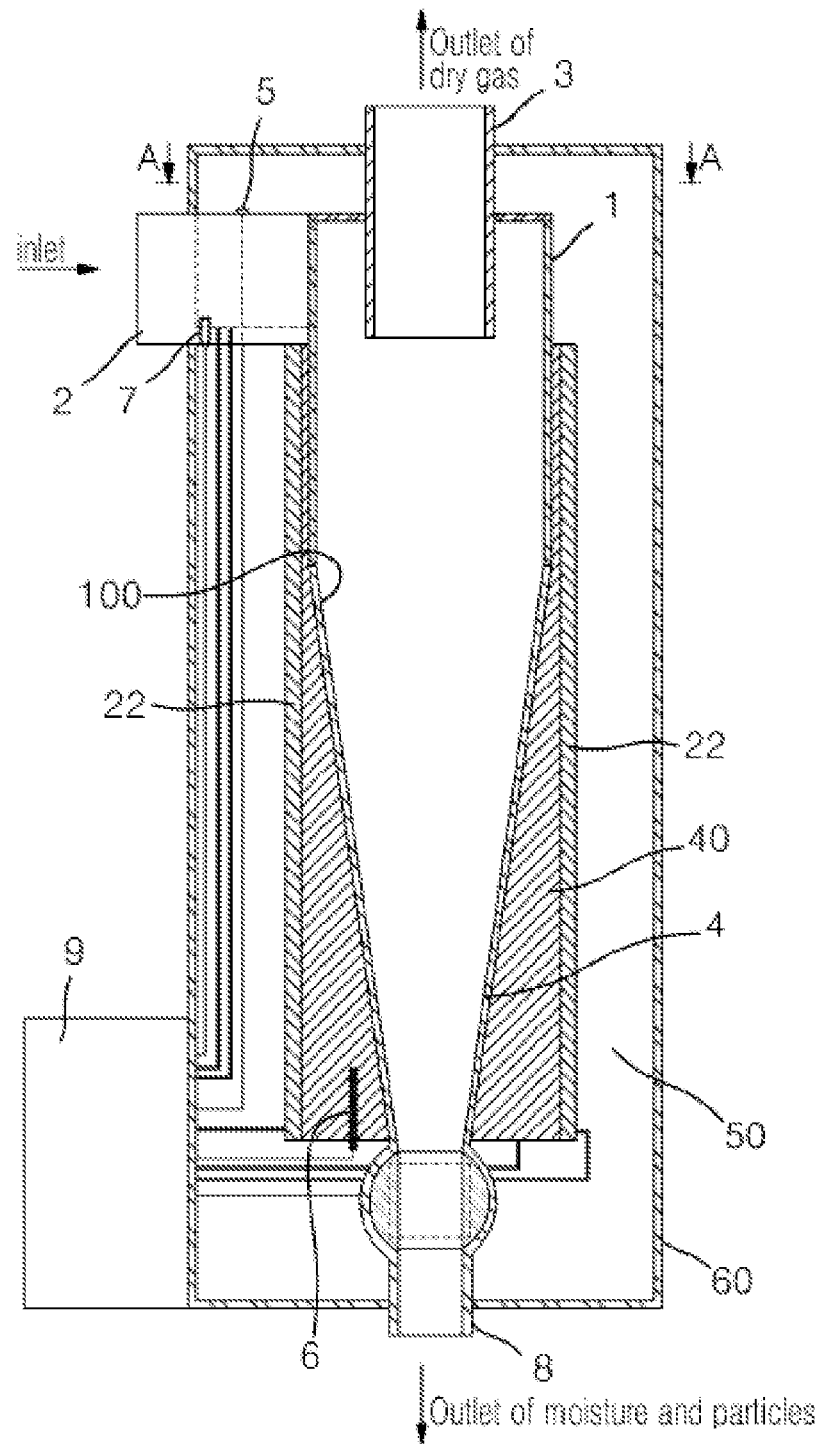
FIG. 1 is a front view illustrating a preprocessing apparatus for measuring and analyzing air pollution according to a first exemplary embodiment of the present invention.

1: Cylindrical portion
2: Inlet pipe
3: Discharge pipe
4: Conical portion
5: Inflow gas temperature sensor
6: Conical portion temperature sensor
7: Humidity sensor
8: Discharge port
9: Controller
21: First cooling Peltier element
22: Second cooling Peltier element
31: Heating Peltier element
40: Block
50: Fiberglass layer
60: Protection box
100: Cyclone main body
110: First opening portion
115: Combustion gas distribution unit 120: Second opening portion
130: Second humidity sensor
200: Cooling and heating block
210: Third cooling Peltier element
220: Second heating Peltier element
230: Cooling and heating block temperature sensor
240: Cylindrical portion
300: Cooling block
310: Fourth cooling Peltier element
320: Cooling block temperature sensor
330: Cylindrical portion
400: Bundle of pipes
500: Socket unit
600: Hood
610: Branch pipe
620: Three-way valve
630: Gas discharge port
640: Liquid discharge port
700: Combustion gas inlet pipe
710: Inflow gas temperature sensor
800: Second protection box
900: Second fiberglass layer

BEST MODE

Hereinafter, configurations of the present invention will be described in more detail with reference to the accompanying drawings. Since the present invention may be variously modified and include various forms, specific exemplary embodiments will be illustrated in the drawings and described in detail.

In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance.

In addition, all terms used herein including technical or scientific terms have the same meanings as meanings which are generally understood by those skilled in the technical field to which the present invention pertains unless they are differently defined. Terms defined in a generally used dictionary shall be construed that they have meanings matching those in the context of a related art, and shall not be construed in ideal or excessively formal meanings unless they are clearly defined in the present application.

Hereinafter, a preprocessing apparatus and a preprocessing method for measuring and analyzing air pollution according to the present invention will be described in detail with reference to the accompanying drawings.

Configuration of First Exemplary Embodiment

Figure 2:
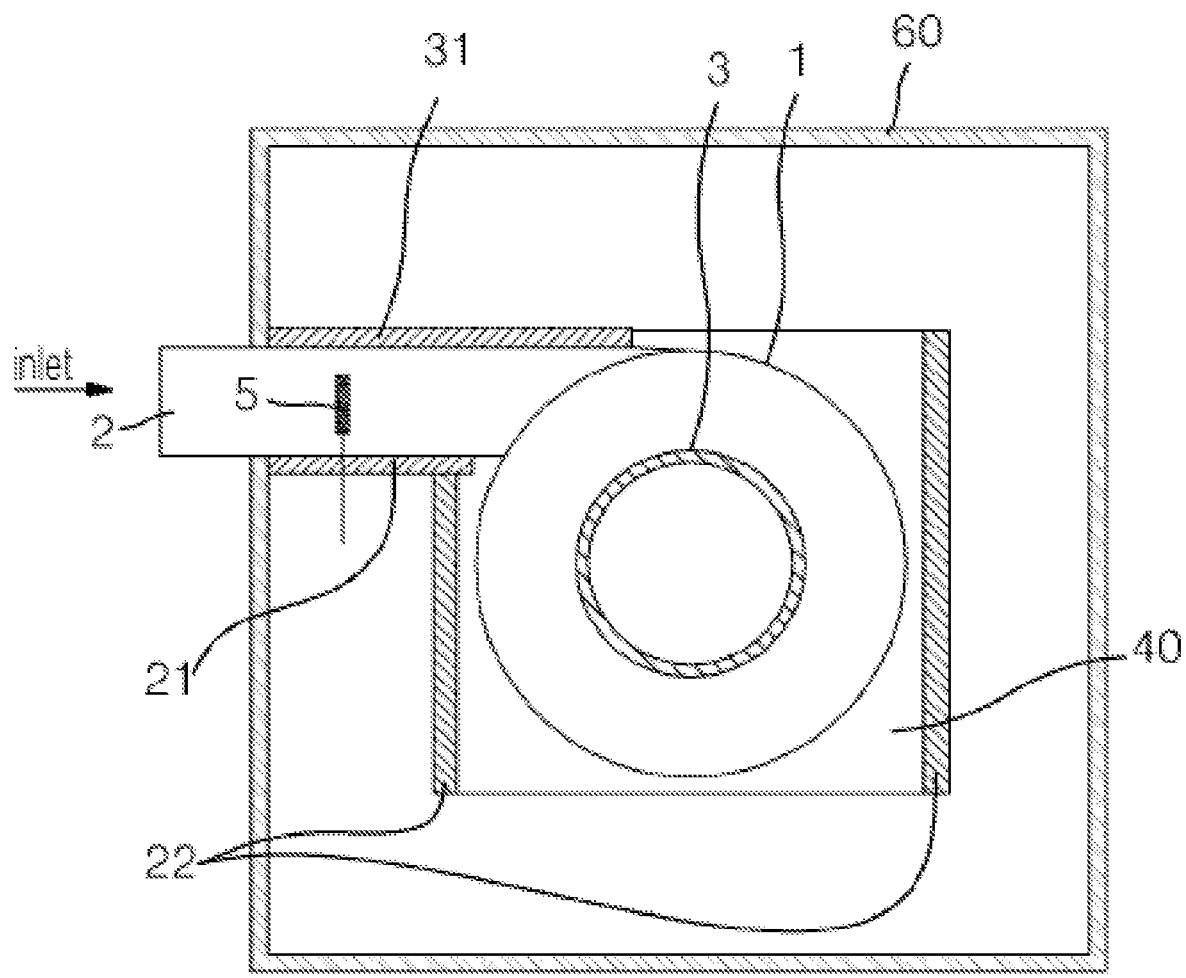
FIG. 2 is a cross-sectional plan view taken along line A-A of FIG. 1 when viewed from the top side.

FIG. 1 is a front view of a preprocessing apparatus for measuring and analyzing air pollution according to a first exemplary embodiment of the present invention, and FIG. 2 is a top plan view when viewed from the top side based on line A-A of FIG. 1. As illustrated in FIGS. 1 and 2, the preprocessing apparatus according to the present invention includes an approximately cyclone main body 100, a cooling means, a heating means, a block 40 made of a thermally conductive material such as aluminum or copper, and a protection box 60.

When describing the respective components in detail, first, the cyclone main body 100 includes: a cylindrical portion 1 which has therein a space portion and disposed vertically; a conical portion 4 which communicate with the cylindrical portion 1 and has a structure, with a wide upper side and a narrow lower side, in which an upper portion has the same diameter as the cylindrical portion 1 so that the upper portion is connected to the cylindrical portion 1, and a diameter is gradually decreased toward a lower portion; a combustion gas inlet pipe 2 which is provided at one side of the cylindrical portion 1 and through the combustion gas including air pollutants to be measured is introduced; and a combustion gas discharge pipe 3 which is positioned at an upper side of a center of the cylindrical portion 1 and guides the preprocessed combustion gas to a pollutant analysis device at a rear end.

In addition, a discharge port 8 is provided at a lower end of the conical portion 4 having the structure with the wide upper side and the narrow lower side, such that moisture and particles contained in the combustion gas to be described below are discharged.

Because the configuration of the cyclone main body 100 is typically and widely known, a further detailed description thereof will be omitted.

One of the main features of the present invention is that in the preprocessing apparatus according to the present invention, a cooling means and a heating means are provided in the combustion gas inlet pipe 2 and cooling means are provided in the cylindrical portion 1 and the conical portion 4 in order to remove moisture and particles contained in the combustion gas introduced into the cyclone main body 100.

Figure 3:
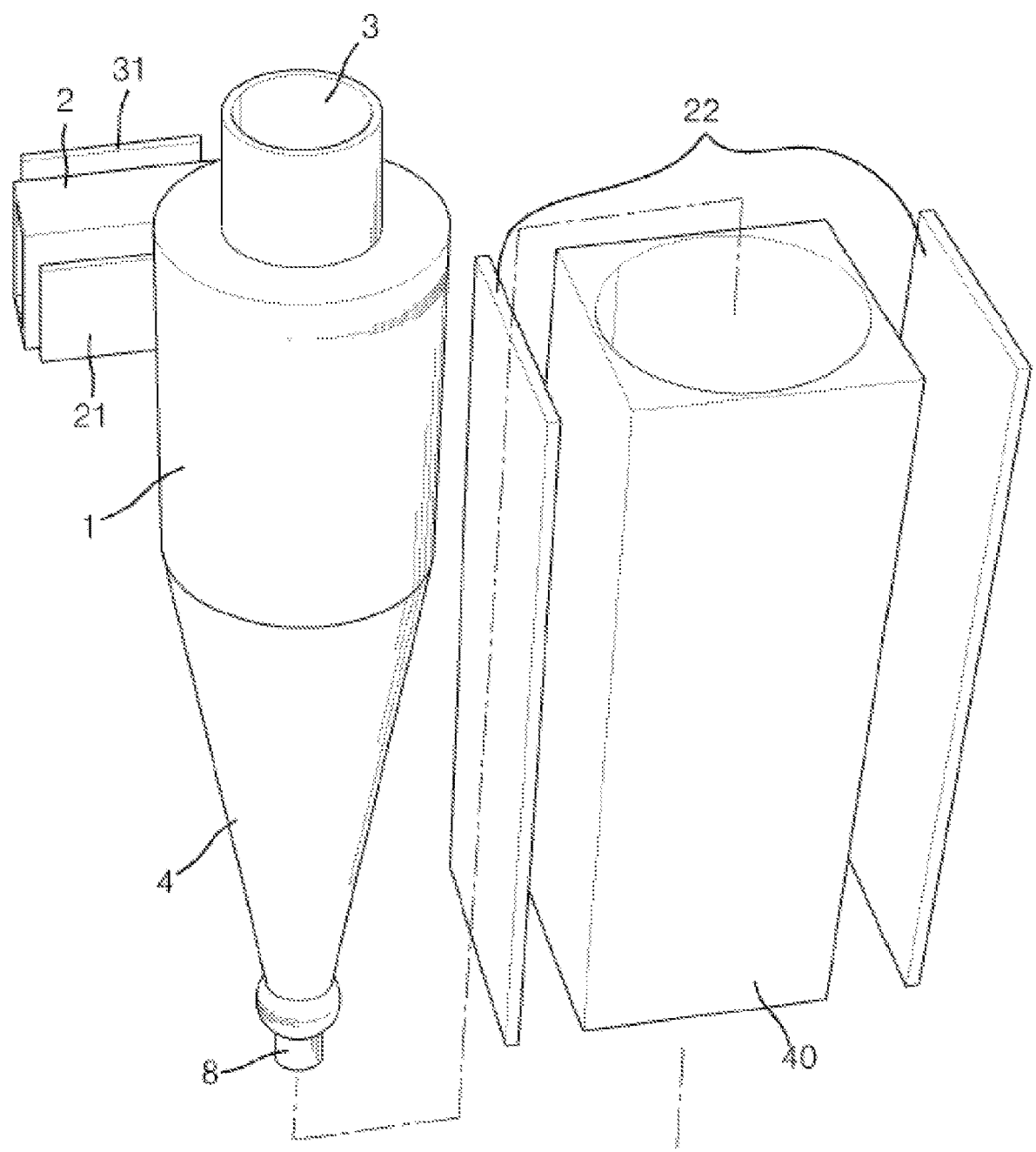
FIG. 3 is an exploded view of the preprocessing apparatus for measuring and analyzing air pollution according to the first exemplary embodiment of the present invention.
Figure 4:
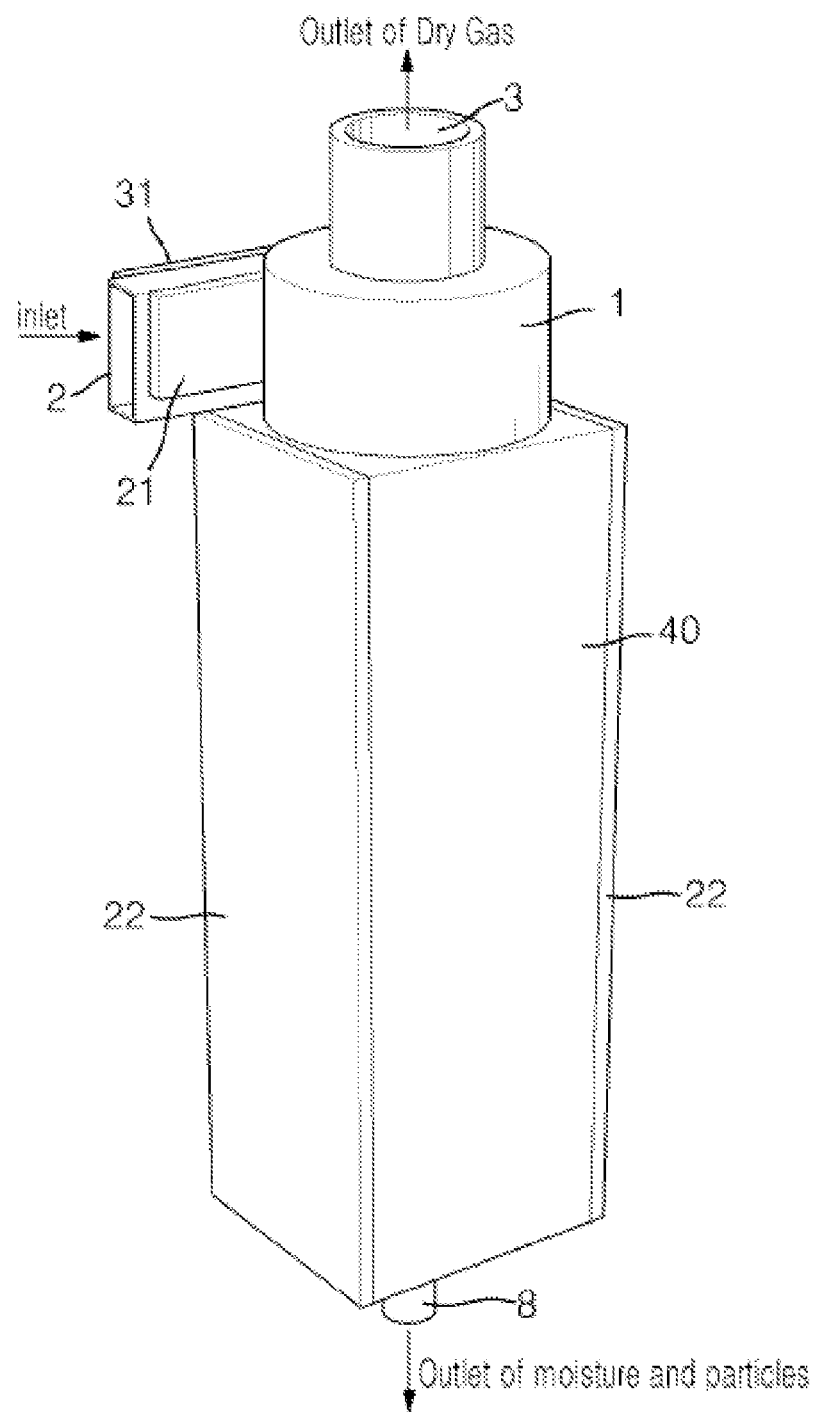
FIG. 4 is a side view of the preprocessing apparatus for measuring and analyzing air pollution according to the first exemplary embodiment of the present invention.

When more specifically describing the cooling means and the heating means, as can be seen from the attached FIGS. 3 and 4, a first cooling Peltier element 21 is provided at one side of the combustion gas inlet pipe 2, and a heating Peltier element 31 is formed at the other side of the combustion gas inlet pipe 2.

Here, the reason why both of the first cooling Peltier element 21 and the heating Peltier element 31 are formed together on the combustion gas inlet pipe 2 is to maintain a temperature of the combustion gas introduced into the inlet pipe 2 within a predetermined range. That is, the reason is that moisture may be condensed if a temperature of the combustion gas is too low, and it is difficult to sufficiently expect the Mpemba effect if a temperature of the combustion gas is too high.

The Mpemba effect means a phenomenon in which high-temperature water is more quickly frozen than low-temperature water in the same condition, and when water molecules are moved to be close to each other, the water molecules attract one another due to a hydrogen bond between the water molecules, and in this case, a covalent bond between a hydrogen atom and an oxygen atom is lengthened, such that energy is accumulated. When the water boils, the hydrogen bond is lengthened and density of water is decreased, and in this case, the covalent bond is decreased again, thereby releasing the accumulated energy. That is, the hot water with a large amount of accumulated energy is quickly frozen because the water more quickly releases energy when the water is cooled.

In addition, second cooling Peltier elements 22 are provided at an outer circumferential edge of the cylindrical portion 1 and the conical portion 4, thereby decreasing a temperature of the introduced combustion gas to −20±10° C. Therefore, the moisture contained in the introduced combustion gas is crystallized by being cooled, and moisture crystals may serve to capture some particles contained in the combustion gas.

Here, the cooling means and the heating means are not particularly limited as long as the cooling means and the heating means are a cooling means (e.g., a cooler) and a heating means (e.g., an electric heater) that may achieve the same function and the same operational effect, but preferably, the cooling means and the heating means may be the first and second cooling Peltier elements 21 and 22 and the heating Peltier element 31 that use the Peltier effect.

The first and second cooling Peltier elements 21 and 22 and the heating Peltier element 31 are devices for cooling or heating a particular local portion by using the Peltier effect, and use a thermoelectric refrigeration principle, that is, a kind of heat pumping phenomenon in which when a circuit is made by joining both ends of two different metal wires and direct current is applied to the circuit, heat is absorbed at one joint portion, and heat is generated at the other joint portion, and the heat absorption and the heat generation occur on the contrary when the direction of electric current is reversed. Therefore, the first and second cooling Peltier elements 21 and 22 and the heating Peltier element 31 using the principle are advantageous in accurately maintaining a temperature of a particular position to a desired temperature.

Meanwhile, the block 40, which is made of aluminum or copper having excellent thermal conductivity and low specific gravity, is disposed at the outer circumferential edges of the cylindrical portion 1 and the conical portion 4, and the block 40 made of aluminum or copper may be designed to be surrounded by the second cooling Peltier elements 22. Here, an inner surface of the block 40 made of aluminum or copper has a shape corresponding to the cylindrical portion 1 and the conical portion 4, but an outer surface of the block 40 has a rectangular parallelepiped shape.

With the aforementioned configuration, quick heat emission may be expected by the second cooling Peltier elements 22, and the second cooling Peltier elements 22 are provided on the outer surface of the block 40 made of aluminum or copper which has a rectangular parallelepiped shape, and as a result, it is possible to easily attach, detach, and repair the second cooling Peltier elements 22.

In addition, the preprocessing apparatus according to the present invention may further include the protection box 60 that accommodates the cyclone main body 100, the cooling means, and the heating means. The protection box 60 serves to protect the cyclone main body 100, the cooling means, and the heating means from external impact, and a space portion between the protection box 60 and the cyclone main body 100 is filled with a fiberglass layer 50 with an excellent thermal insulation effect. Therefore, it is possible to not only maintain a temperature of the conical portion 4 to −20±10° C. by the second cooling Peltier elements 22, and but also prevent heat exchange with the outside, thereby efficiently managing energy.

Here, an inflow gas temperature sensor 5 is provided at one side of the inlet pipe 2 in order to measure a temperature of combustion gas including air pollutants, and a conical portion temperature sensor 6 is further provided to measure a temperature of the conical portion 4. The inflow gas temperature sensor 5 and the conical portion temperature sensor 6 serve to maintain a temperature of the introduced gas and a temperature of gas in the conical portion 4 to a desired range, thereby maximizing an effect of removing moisture and particles contained in combustion gas.

The attached drawings illustrate the two temperature sensors, but it is obvious to those skilled in the art that the number of installed sensors or the installation positions may be variously modified as necessary.

In addition, in the present invention, a humidity sensor 7 may be provided at one side of the inlet pipe 2 in order to recognize humidity of the combustion gas containing air pollutants.

That is, the humidity sensor 7 decreases a flow rate of combustion gas if humidity of the introduced combustion gas is equal to or higher than a predetermined reference value, and increases a flow rate of combustion gas if humidity is equal to or lower than the predetermined reference value, and as a result, it is possible to allow moisture crystals to be uniformly formed on an inner wall surface of the cyclone main body by increasing and decreasing a flow rate of combustion gas in response to humidity of the introduced combustion gas.

In addition, the preprocessing apparatus according to the present invention may further include a controller 9 capable of controlling and adjusting the temperature sensors 5 and 6, the humidity sensor 7, the cooling means, the heating means, and the like. The controller 9 may be a microcomputer, a CPU, or the like.

Operation of First Exemplary Embodiment

Figure 5:
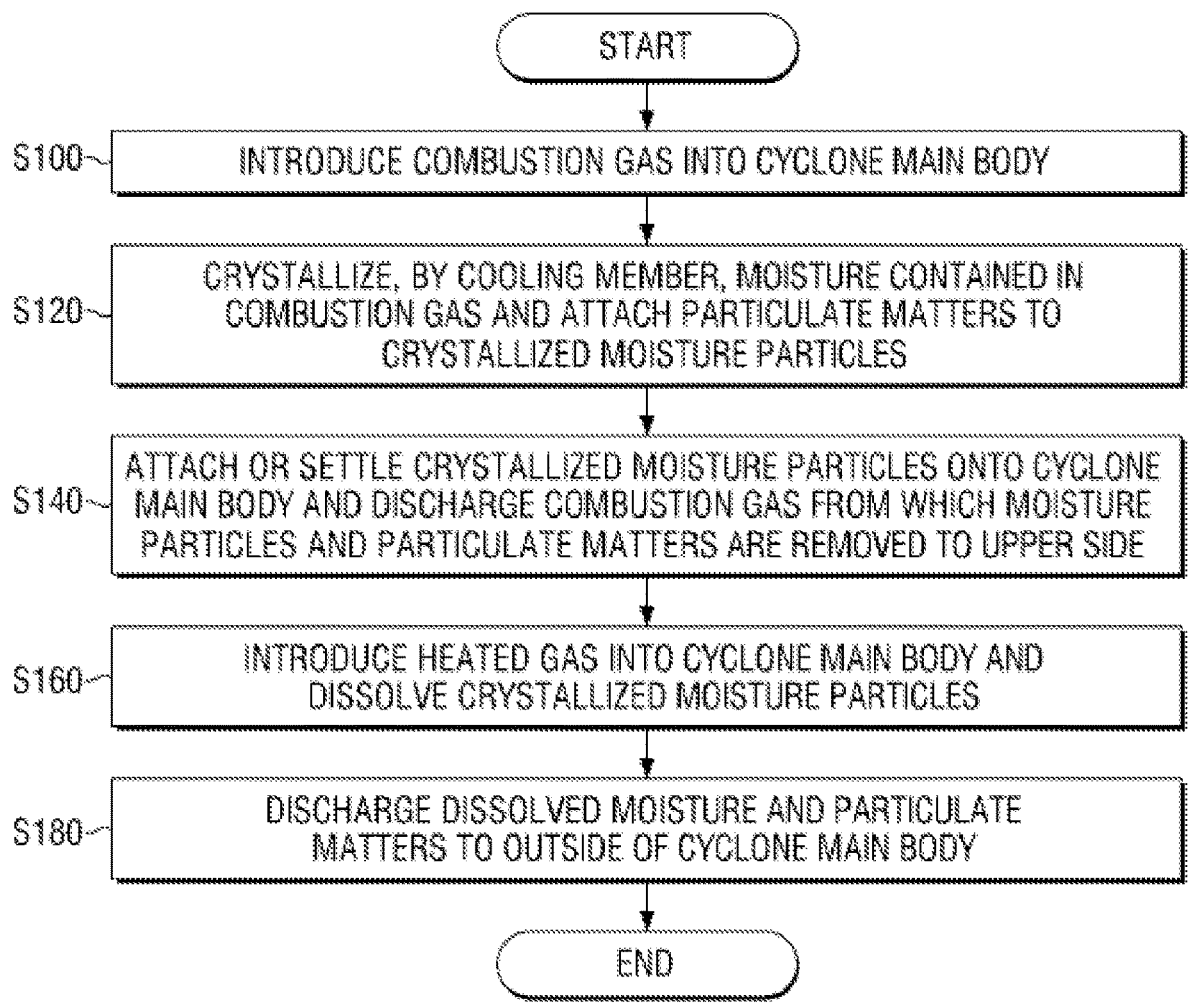
FIG. 5 is a flowchart for explaining a preprocessing method for measuring and analyzing air pollution according to the first exemplary embodiment of the present invention.

Hereinafter, a preprocessing method for measuring and analyzing air pollution according to the first exemplary embodiment of the present invention will be described with reference to the attached FIG. 5.

The preprocessing method according to the first exemplary embodiment of the present invention includes: introducing combustion gas, which needs to be preprocessed, into the cyclone main body 100 (S100); crystallizing moisture contained in the combustion gas by cooling the moisture by a cooling means and attaching some particulate matters to crystallized moisture particles (S120); attaching or settling the crystallized moisture particles and the particulate matters onto the cyclone main body 100 and discharging the combustion gas from which the moisture is removed (S140); introducing heated gas into the cyclone main body 100 and dissolving the crystallized moisture particles (S160); and discharging the dissolved moisture and the particulate matters to the outside (S180).

When describing the preprocessing method in detail, to remove moisture and particles which are contained in the combustion gas and act as interfering substances when measuring and analyzing air pollution, the combustion gas is introduced into the combustion gas inlet pipe 2 provided at one side of the cylindrical portion 1 that constitutes the cyclone main body 100.

Here, a temperature of the combustion gas being introduced may be maintained at 70±10° C. That is, the reason is that moisture may be condensed if a temperature of the combustion gas is too low, and it is difficult to sufficiently expect the Mpemba effect if a temperature of the combustion gas is too high.

In addition, the adjustment of the temperature of the combustion gas may be implemented by the first cooling Peltier element 21 disposed at one side of the inlet pipe 2 and the heating Peltier element 31 disposed at the other side.

After the temperature of the combustion gas is adjusted to the range of 70±10° C. as described above, the introduced combustion gas is cooled by using the cooling means provided at the outer circumferential edge of the cylindrical portion 1 and the outer circumferential edge of the conical portion 4 at the lower side of the cylindrical portion 1. Here, a cooling temperature by the cooling member 20 may be maintained at −20±10° C., and within the temperature range, the moisture in a vaporized state is crystallized, flows along with a flow of gas in the cyclone, and then is attached to the inner wall surface of the cylindrical portion 1 or the inner wall surface of the conical portion 4. In addition, as the crystallized moisture particles collide with the particulate matters, some particulate matters are attached to moisture crystals.

Of course, even though the moisture crystals or the particulate matters are not attached to the inner wall surface of the cylindrical portion 1 or the inner wall surface of the conical portion 4, the moisture crystals or the particulate matters, which are not attached to the inner wall surface of the cylindrical portion 1 or the inner wall surface of the conical portion 4, may be removed through the discharge port 8 provided at the lower side of the conical portion 4 because of the properties of the cyclone device that makes a swirling flow of a fluid, applies centrifugal force to particles contained in the fluid, and then separates and captures the particles from the liquid.

Meanwhile, to remove the moisture crystals attached to the inner wall surface of the cylindrical portion 1 or the conical portion 4, warm gas may be supplied in a reverse direction through the combustion gas inlet pipe 2.

Here, the cooling means and the heating means are not particularly limited as long as the cooling means and the heating means are a cooling means and a heating means that may achieve the same function and the same operational effect, but preferably, the cooling means and the heating means may be the first and second cooling Peltier elements 21 and 22 and the heating Peltier element 31 that use the Peltier effect.

As described above, the present invention may provide the preprocessing apparatus and the preprocessing method for measuring and analyzing air pollution, which are capable of removing particulate matters as well as moisture contained in combustion gas by cooling the combustion gas introduced into the cyclone main body.

Configuration of Second Exemplary Embodiment

Figure 6:
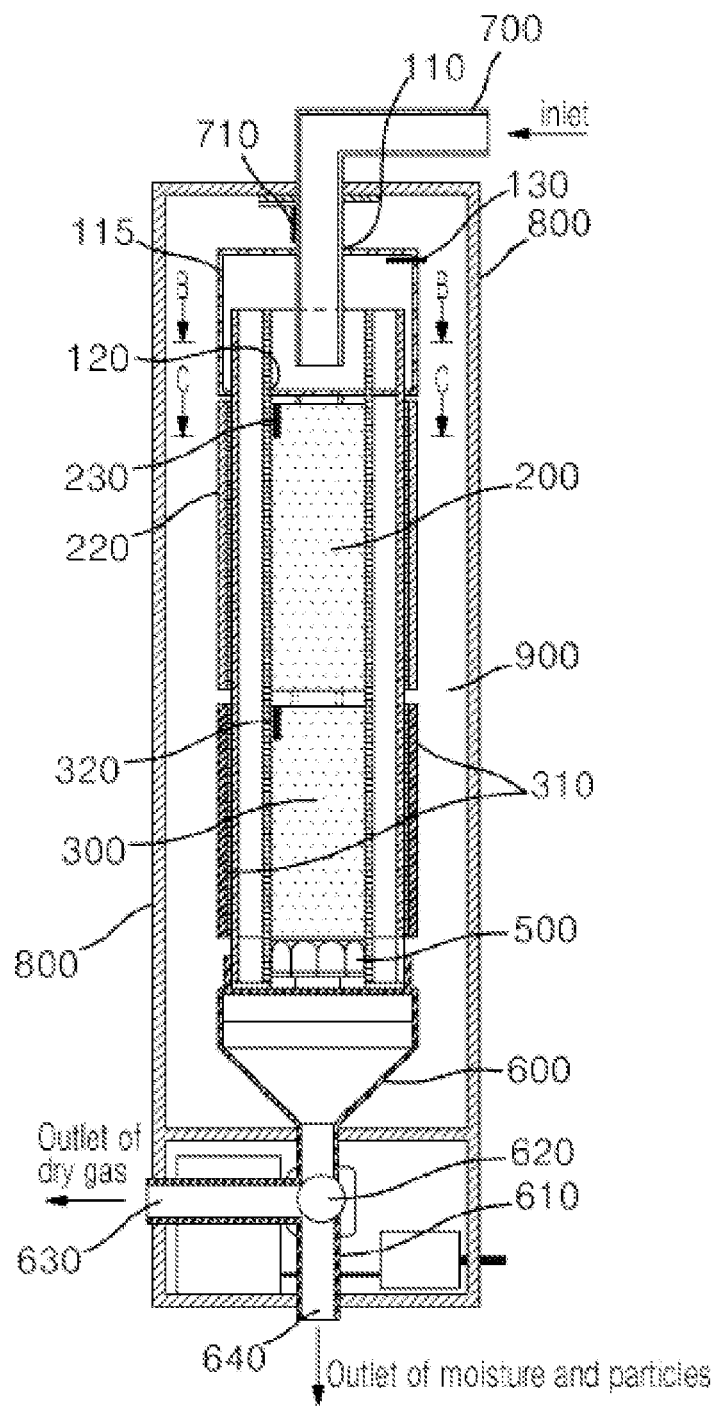
FIG. 6 is a cross-sectional front view of a preprocessing apparatus according to a second exemplary embodiment of the present invention.
Figure 7:
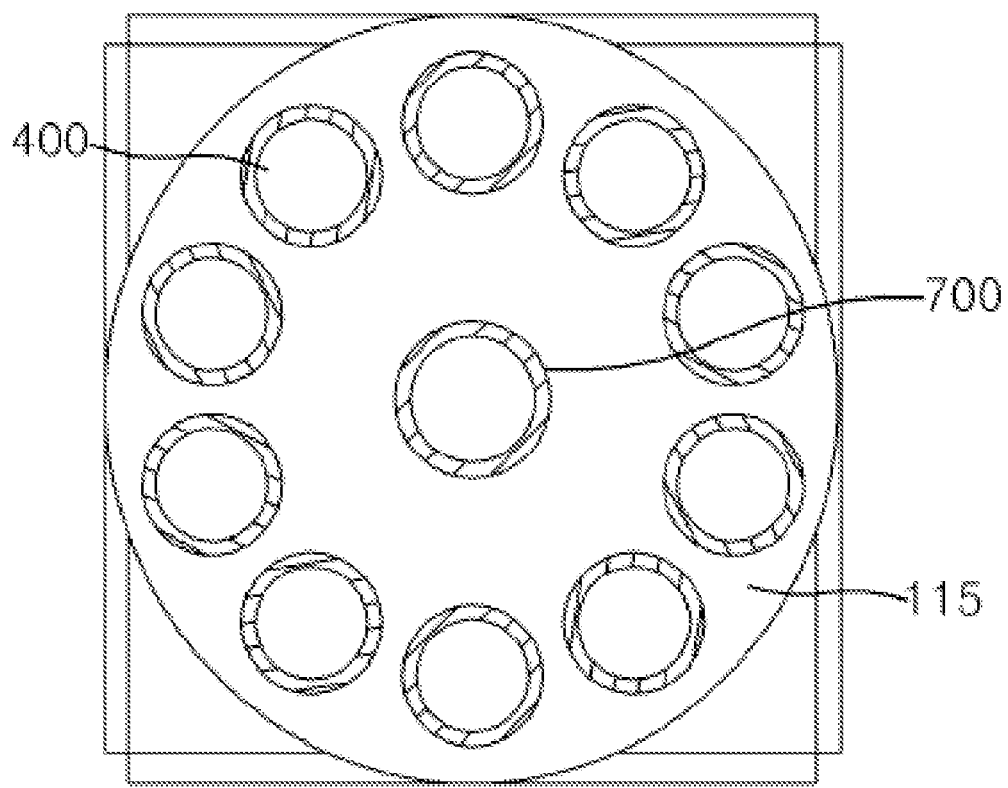
FIG. 7 is a cross-sectional view taken along line B-B of FIG. 6.
Figure 8:
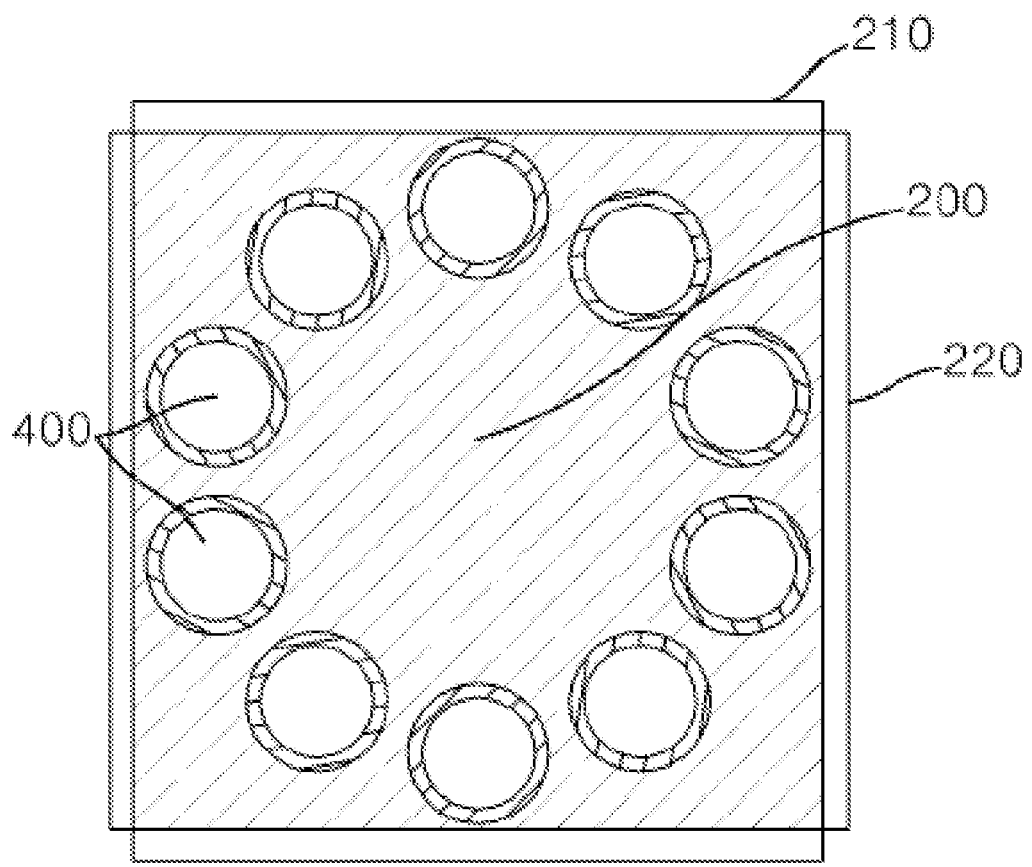
FIG. 8 is a cross-sectional view taken along line C-C of FIG. 6.
Figure 9:
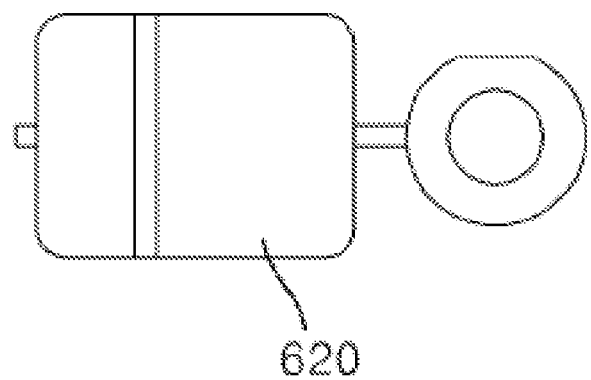
FIG. 9 is a side view of a three-way valve 620 illustrated in FIG. 6.
Figure 10:
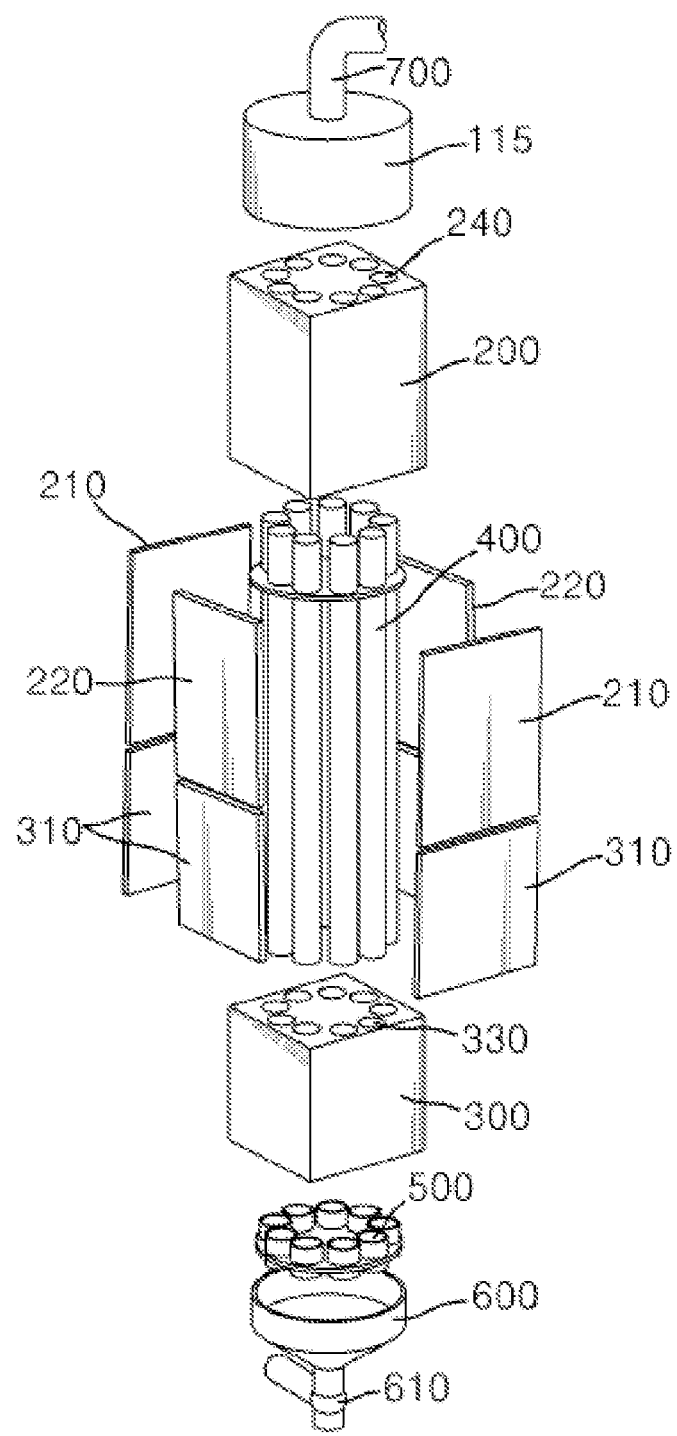
FIG. 10 is an exploded perspective view of the preprocessing apparatus according to the second exemplary embodiment of the present invention.
Figure 11:
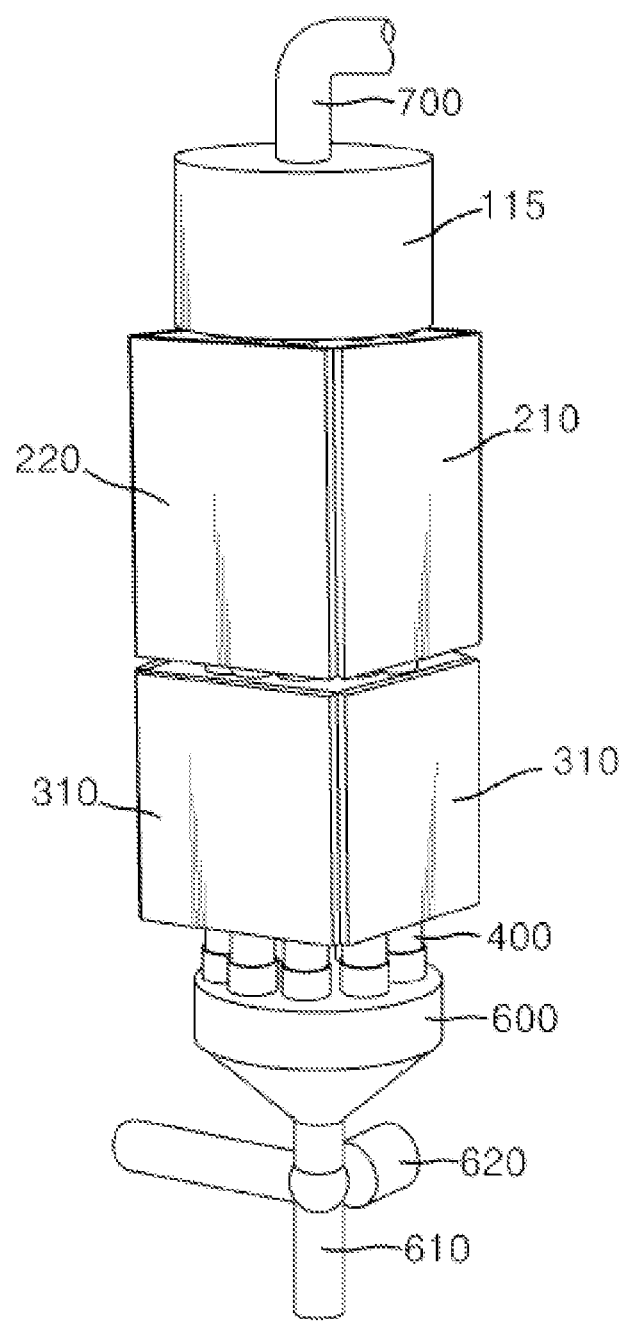
FIG. 11 is an assembled view of the exploded perspective view illustrated in FIG. 10.
Figure 12:
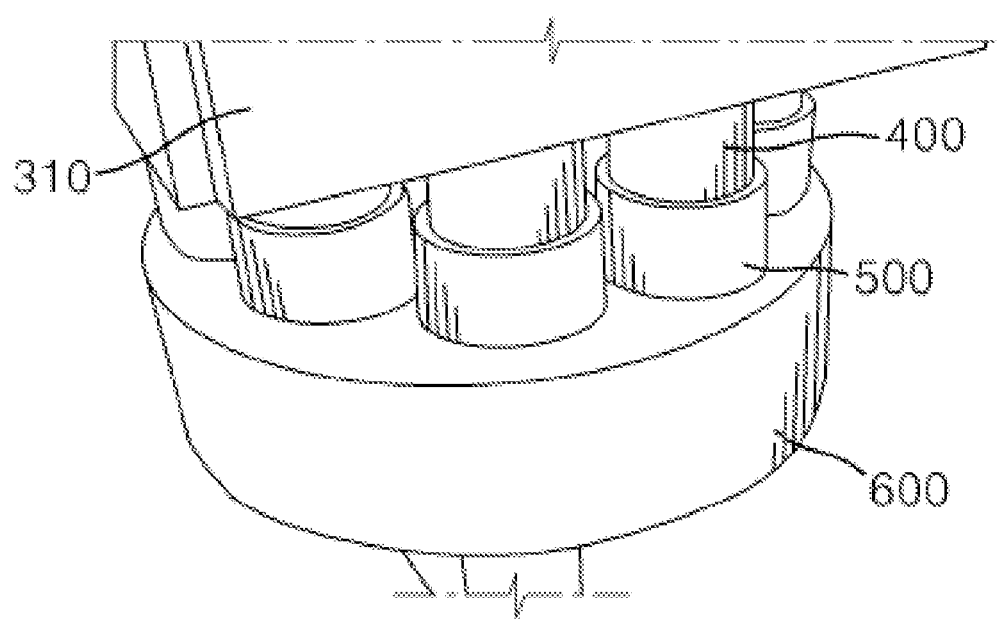
FIG. 12 is an enlarged view of a socket unit and a hood unit of the preprocessing apparatus according to the second exemplary embodiment of the present invention.

FIG. 6 is a cross-sectional front view of a preprocessing apparatus according to a second exemplary embodiment of the present invention, FIG. 7 is a cross-sectional view taken along line B-B of FIG. 6, FIG. 8 is a cross-sectional view taken along line C-C of FIG. 6, FIG. 9 is a side view of a three-way valve 620 illustrated in FIG. 6, FIG. 10 is an exploded perspective view of the preprocessing apparatus according to the second exemplary embodiment of the present invention, FIG. 11 is an assembled view of the exploded perspective view illustrated in FIG. 10, and FIG. 12 is an enlarged view of a socket unit and a hood unit of the preprocessing apparatus according to the second exemplary embodiment of the present invention.

As illustrated in FIGS. 6 to 12, when describing the preprocessing apparatus according to the second exemplary embodiment of the present invention, the preprocessing apparatus according to the present invention includes a combustion gas distribution unit 115, a cooling and heating block 200, a cooling block 300, a bundle of pipes 400, a socket unit 500, a hood 600, and a combustion gas inlet pipe 700.

When describing the respective components in detail, first, the combustion gas distribution unit 115 has a vacant cylindrical shape, a first opening portion 110 into which the combustion gas inlet pipe 700 to be described below is inserted and mounted is formed in an upper portion of the combustion gas distribution unit 115, and a plurality of second opening portions 120, which has the number and a size corresponding to the number of pipes and the size of the bundle of pipes 400, is provided in a lower surface of the combustion gas distribution unit 115 so that the bundle of pipes 400 to be described below may be inserted and mounted into the plurality of second opening portions 120.

Therefore, combustion gas conveyed to the combustion gas inlet pipe 700 is supplied to the combustion gas distribution unit 115, and then uniformly distributed into the bundle of pipes 400 inserted into the combustion gas distribution unit 115, such that the combustion gas flows to the cooling and heating block 200 and the cooling block 300 which will be described below.

The cooling and heating block 200 is positioned at a bottom side of the combustion gas distribution unit 115, a plurality of elongated cylindrical spaces is formed in the cooling and heating block 200, and heating members and cooling members capable of performing heating or cooling are added to the outside of the cooling and heating block 200. In addition, a cooling and heating block temperature sensor 230 is provided inside the bundle of pipes 400 in order to measure a temperature of the combustion gas in the bundle of pipes 400 being in contact with the cooling and heating block 200.

That is, as illustrated in FIG. 10 in detail, third cooling Peltier elements 210, which are the cooling members, are provided on two opposite outer surfaces of the cooling and heating block 200, and second heating Peltier elements 220, which are the heating members, are provided on the remaining two surfaces to which the third cooling Peltier elements 210 are not attached. The reason why the third cooling Peltier element 210 and the second heating Peltier element 220 are provided together as described above is to operate the second heating Peltier element 220 to heat the combustion gas when a temperature of the combustion gas in the bundle of pipes 400 being in contact with the cooling and heating block 200 is lower than a predetermined temperature, and to operate the third cooling Peltier element 210 to lower a temperature of the combustion gas when the temperature of the combustion gas is higher than the predetermined temperature on the contrary, and as a result, it is possible to adjust the temperature of the combustion gas within a predetermined range.

As a second exemplary embodiment, a cooling function is performed when a temperature of the introduced combustion gas is equal to or higher than 80° C., and a heating function is performed when a temperature of inflow gas is equal to or lower than 60° C. Here, the cooling member and the heating member are described as being the cooling Peltier element and the heating Peltier element that use the Peltier effect, but the cooling member and the heating member are not particularly limited as long as the cooling or heating member is a cooling or heating means capable of achieving the same function and the same operational effect.

The cooling block 300 has the same shape and the same structure as the cooling and heating block 200, but only a difference between the cooling block 300 and the cooling and heating block 200 is that only fourth cooling Peltier elements 310, which are the cooling members, are provided on an outer circumferential surface of the cooling block 300.

That is, the cooling block 300 only serves to perform a function of cooling the combustion gas in the bundle of pipes 400 being in contact with the cooling block 300 within a predetermined temperature range, and a cooling block temperature sensor 320 for measuring a temperature of the combustion gas is provided inside the bundle of pipes 400 being in contact with the cooling block 300.

Here, the reason why the cooling and heating block 200 and the cooling block 310 are separately provided is to quickly crystallize moisture contained in the combustion gas by using the Mpemba effect.

In the present invention made in consideration of the Mpemba effect, the combustion gas is heated by maintaining a high-temperature condition in the cooling and heating block 200, and the combustion gas is cooled by the cooling block 300 to the extent that the moisture contained in the combustion gas may be crystallized, thereby removing the moisture contained in the combustion gas.

Meanwhile, materials and shapes of the cooling and heating block 200 and the cooling block 300 are not particularly limited, the cooling and heating block 200 and the cooling block 300 may be made of a material such as aluminum or copper with excellent thermal conductivity and low specific gravity in order to effectively receive and transfer heat from/to the heating member and the cooling member being in contact with the cooling and heating block 200 and the cooling member being in contact with the cooling block 300, and the cooling and heating block 200 and the cooling block 300 may have a rectangular parallelepiped shape in consideration of easy of attachment, detachment, and repair of the heating member and the cooling member.

Meanwhile, the bundle of pipes 400 serves to allow the combustion gas distributed from the combustion gas distribution unit 115 to flow therethrough, and performs a function of crystallizing moisture in the combustion gas based on the Mpemba effect, and removing the crystallized particles.

In more specifically, the bundle of pipes 400 is an assembly of a plurality of pipes, and the bundle of pipes 400 is inserted into cylindrical portions 240 and 330 of the cooling and heating block 200 and the cooling block 300. In addition, upper end portions of the pipes are inserted into the second opening portions 120 of the combustion gas distribution unit 115 such that the combustion gas is introduced into the pipes, and lower end portions of the pipes are coupled to the socket unit 500 to be described below.

Meanwhile, the number of pipes of the bundle of pipes 400 are not limited and may be determined in consideration of a flow rate of the introduced combustion gas, a diameter of the pipe, a length of the pipe, and the like, and the pipe may not only be made of aluminum or copper with excellent thermal conductivity, but also be made of quartz or the like with low reactivity with the gas to be measured.

Next, when describing the configurations of the socket unit 500 and the hood 600 with reference to FIG. 12, the socket unit 500 accommodates the lower end portions of the bundle of pipes 400 which protrude to the outside of the cooling block 300, and the socket unit 500 has a sealed structure coupled to the hood 600.

That is, to measure pollutants contained in the combustion gas, a sealed structure is required so that the entire amount of combustion gas may be conveyed to a measurement device via the bundle of pipes 400, and the socket unit 500 performs a sealing function by connecting the hood 600 and the bundle of pipes 400.

Meanwhile, a '⊣'-shaped branch pipe 610 and a three-way valve 620 are installed on the hood 600 connected to the socket unit 500 in order to change a flow of gas.

That is, opening and closing directions of the three-way valve 620 are adjusted so that the combustion gas communicates with the gas discharge port 630 when introducing the combustion gas, from which moisture is removed, into the measurement device, and the combustion gas communicates with a liquid discharge port 640 when removing moisture crystals attached in the bundle of pipes 400. Here, as a method of removing the moisture crystals attached in the bundle of pipes 400, high-temperature gas may be injected into the bundle of pipes 400 or gas heated to a predetermined temperature by the cooling and heating block 200 may be used.

In addition, in the present invention, a second humidity sensor 130 is further provided in an internal space of the combustion gas distribution unit 115 in order to recognize humidity of the combustion gas introduced into the combustion gas distribution unit 115. That is, the second humidity sensor 130 decreases a flow rate of combustion gas if humidity of the introduced combustion gas is equal to or higher than a predetermined reference value, and increases a flow rate of combustion gas if humidity is equal to or lower than the predetermined reference value, and as a result, it is possible to allow moisture crystals to be uniformly formed on an inner wall surface of the bundle of pipes by increasing and decreasing a flow rate of combustion gas in response to humidity of the introduced combustion gas.

The second exemplary embodiment of the present invention is related to the preprocessing apparatus using the Mpemba effect, it is very important to control the combustion gas flowing in the bundle of pipes 400 within a predetermined range, and the bundle of pipes 400 needs to be protected from external impact in order to prevent a leak of combustion gas. Therefore, a second protection box 800 is installed to protect the combustion gas distribution unit 115, the cooling and heating block 200, the cooling block 300, and the hood 600 from external impact, and a second fiberglass layer 900, which has an excellent thermal insulation effect, is installed in the second protection box 800 in order to maximally inhibit heat transfer to the outside.

Operation of Second Exemplary Embodiment

Figure 13:
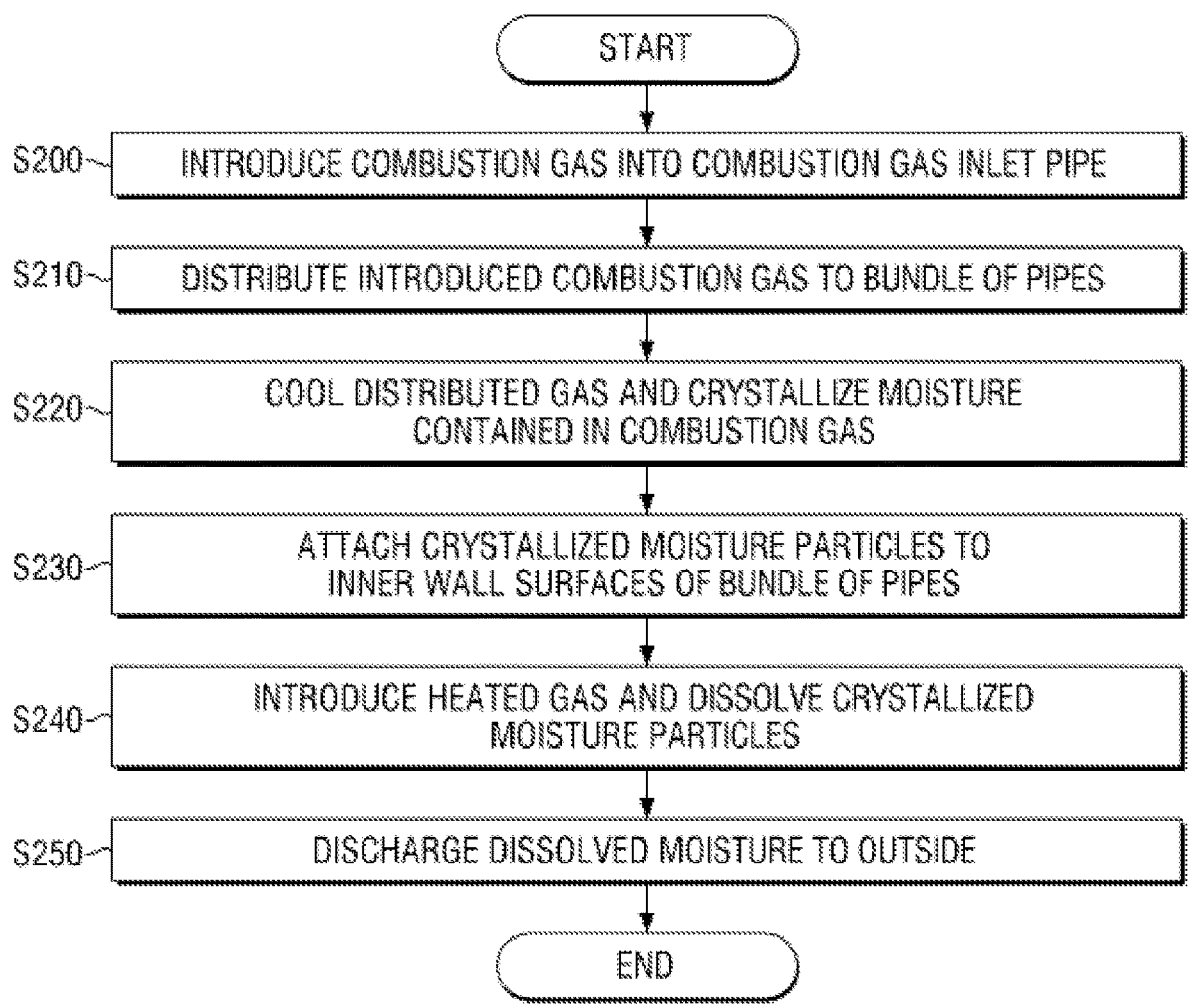
FIG. 13 is a flowchart for explaining a preprocessing method for measuring and analyzing air pollution according to the second exemplary embodiment of the present invention.

Hereinafter, a preprocessing method for measuring and analyzing air pollution according to the second exemplary embodiment of the present invention will be described with reference to the attached FIG. 13.

The preprocessing method according to the second exemplary embodiment of the present invention includes: a first step of introducing combustion gas into the combustion gas inlet pipe 700 (S200); a second step of distributing the introduced combustion gas into the bundle of pipes 400 (S210); a third step of cooling the distributed gas and crystallizing moisture contained in the combustion gas (S220); a fourth step of attaching the crystallized moisture particles to inner wall surfaces of the bundle of pipes 400 (S230); a fifth step of introducing heated gas and dissolving the crystallized moisture particles attached to the inner wall surfaces of the bundle of pipes 400 (S240); and a sixth step of discharging the dissolved moisture to the outside (S250).

When describing the configuration of the preprocessing method in detail, combustion gas to be measured is introduced into the combustion gas inlet pipe 700 in order to remove moisture contained in the combustion gas which acts as an interfering substance when measuring and analyzing air pollution.

Then, the combustion gas flows by being uniformly distributed into the bundle of pipes 400 made by assembling the plurality of pipes which is inserted and mounted into the cylindrical portions of the cooling and heating block 200 and the cooling block 300 and communicates with the combustion gas distribution unit 115. In this case, the cooling member and the heating member provided on the outer surface of the cooling and heating block 200 operate so that a temperature of the combustion gas is adjusted within a predetermined range, and then the cooling member provided outside the cooling block 300 operates to cool the combustion gas. Here, the cooling member and the heating member are variably operated so that a temperature of the combustion gas introduced into the cooling and heating block 200 is maintained at 70±10° C., and a temperature of the combustion gas in the cooling block 300 is maintained at −20±10° C.

As described above, moisture crystals are then formed while the moisture heated by the cooling and heating block 200 based on the Mpemba effect passes through the cooling block 300, and the moisture crystals are attached to the inner wall surfaces of the bundle of pipes 400, such that the moisture in the combustion gas is removed.

In addition, the moisture crystals, which are formed while the moisture passes through the cooling block 300, may be formed while capturing some particles contained in the combustion gas, and particles may be captured by the moisture crystals attached to the wall surfaces, such that the removal of some particles contained in the combustion gas may be expected.

It is difficult to expect a sufficient Mpemba effect because moisture is condensed or there is a small temperature difference from the cooling block 300 if a temperature of the combustion gas in the cooling and heating block 200 is lower than 60° C., and it is also difficult to expect a sufficient Mpemba effect because energy is unnecessarily consumed and there is a small temperature difference from the cooling block 300 if the temperature of the combustion gas is higher than 80° C.

Meanwhile, it is necessary to adjust a temperature of the combustion gas within an appropriate range because an area of ice crystals produced in the Peltier element is decreased if a temperature of the combustion gas in the cooling block 300 is higher than −10° C., and because a loss of targeted gas components occurs and a large amount of energy is required, which causes inefficiency, if the temperature of the combustion gas is lower than −30° C.

If the moisture crystals, which are produced through the aforementioned process, are continuously attached to the inner wall surfaces of the bundle of pipes 400, diameters of the bundle of pipes 400 are decreased, and as a result, pressure applied to the combustion gas inlet pipe 700 may be increased or cooling efficiency of the cooling block 300 may deteriorate. Therefore, it is necessary to remove the moisture crystals attached in the bundle of pipes 400. The removal of the moisture crystals may be achieved by injecting high-temperature gas into the bundle of pipes 400 after switching the three-way valve 620 or injecting gas heated to a predetermined temperature by the cooling and heating block 200.

As described above, the present invention may provide the preprocessing apparatus and the preprocessing method for measuring and analyzing air pollution, in which the cooling member or the cooling and heating members are provided outside the cooling and heating block 200 and the cooling block 300, thereby removing moisture contained in the combustion gas by quickly decreasing a temperature of the combustion gas.

While the present invention has been described with reference to the aforementioned exemplary embodiments, those skilled in the art can easily recognize that various other modifications and alterations may be made without departing from the subject matter and the scope of the present invention, and it is apparent that all of these modifications and alterations fall within the appended claims.

The invention claimed is:

1. A preprocessing method for measuring and analyzing air pollution, the preprocessing method comprising:
   introducing combustion gas including air pollutants to be measured into a cyclone main body;
   crystallizing moisture particles contained in the combustion gas by cooling the moisture by a cooling means provided at an outer circumferential edge of the cyclone main body, and attaching particulate matters to the crystallized moisture particles;
   attaching or settling the crystallized moisture particles and the particulate matters attached to the crystallized moisture particles onto a wall surface at an inner circumferential edge of the cyclone main body, and discharging the combustion gas, from which the moisture particles and the particulate matters are removed, to an upper side of the cyclone main body;
   introducing heated gas into the cyclone main body and dissolving the crystallized moisture particles attached to the wall surface at the inner circumferential edge of the cyclone main body; and
   discharging the dissolved crystallized moisture particles and the particulate matters to an outside of the cyclone main body.

2. The preprocessing method of claim 1, wherein the particulate matters, which are contained in the combustion gas and are not attached to the crystallized moisture particles, are settled based on a cyclone principle.

3. The preprocessing method of claim 1, wherein the cooling means provided at the outer circumferential edge of the cyclone main body is a second cooling Peltier element, and a cooling temperature is −20±10° C.

4. The preprocessing method of claim 1, wherein in the introducing of the combustion gas into the cyclone main body, a temperature of the combustion gas is maintained at 70±10° C., and a temperature range is adjusted by a first cooling Peltier element provided at one side of an inlet pipe and a heating Peltier element provided at another side of the inlet pipe.

* * * * *